United States Patent [19]

Willmund et al.

[11] Patent Number: 4,765,875
[45] Date of Patent: Aug. 23, 1988

[54] PREPARATION OF SULFONATED LUBRICATING AGENTS FOR LEATHER AND FURS

[75] Inventors: Wolf-Dieter Willmund, Düsseldorf; Jürgen Plapper, Hilden; Friedrich Pieper, Langenfeld; Jochen Heidrich, Düsseldorf, all of Fed. Rep. of Germany

[73] Assignee: Henkel Kommanditgesellschaft auf Aktien, Düsseldorf-Holthausen, Fed. Rep. of Germany

[21] Appl. No.: 527,316

[22] Filed: Aug. 29, 1983

Related U.S. Application Data

[63] Continuation of Ser. No. 259,526, May 1, 1981, abandoned.

[30] Foreign Application Priority Data

May 12, 1980 [DE] Fed. Rep. of Germany ......... 308176

[51] Int. Cl.$^4$ ............................................. C07C 143/90
[52] U.S. Cl. ............................. 204/157.79; 260/400; 260/401
[58] Field of Search ................ 260/400, 401; 204/161, 204/157.79

[56] References Cited

U.S. PATENT DOCUMENTS

| Re. 20,968 | 1/1939 | Reed et al. | 260/400 |
|---|---|---|---|
| 2,046,090 | 6/1936 | Reed | 204/157.79 |
| 2,344,154 | 3/1944 | Lighthipe | 260/400 |
| 3,300,525 | 1/1967 | Plapper et al. | 260/400 |
| 3,354,187 | 11/1967 | Stein et al. | 260/400 |
| 3,370,005 | 2/1968 | Stein et al. | 252/8.57 |
| 3,724,999 | 4/1973 | Stein et al. | 8/94.22 |
| 3,988,247 | 10/1976 | Dieckelmann et al. | 252/8.7 |

FOREIGN PATENT DOCUMENTS

| 1946723 | 9/1978 | Fed. Rep. of Germany . |
|---|---|---|
| 2245077 | 8/1979 | Fed. Rep. of Germany . |
| 849393 | 11/1939 | France . |
| 870294 | 3/1942 | France . |
| 2031167 | 11/1970 | France . |
| 538407 | 8/1941 | United Kingdom . |
| 339543 | 6/1969 | U.S.S.R. . |

OTHER PUBLICATIONS

Derwent Abstract 4623, 6-2-69 (Soviet Union 339,543).
Volkov, Y. M., et al, "Method of Obtaining Monochloroan Hydrides of Sulfocarboxylic Acids" (English Translation of Soviet Union 339, 543).
*Ullmans Encyklopaie der technischen Chemie*, Munich (1965), p. 562.
*Methoden der Organischen Chemie*, Stuttgart (1955), pp. 411-414.
*Methoden der Organischen Chemie*, Stuttgart (1975), p. 168.
*Handbuch der Gerbereichemie und Lederfabrikation*, Vienna (1961), pp. 1679-1680.
*Tetrahedron Letters*, No. 27, Pergamon Press (1966), pp. 3095-3103.
A. J. Stirton, "α-Sulfo Fatty Acids and Derivatives, Synthesis, Properties and Use", *The Journal of American Oil Chemists' Society*, vol. 39, pp. 490-496.

*Primary Examiner*—Charles F. Warren
*Attorney, Agent, or Firm*—Kane, Dalsimer, Sullivan, Kurucz, Levy, Eisele & Richard

[57] ABSTRACT

This invention relates to sulfonated lubricating agents for leather and furs. More specifically, this invention relates to a process for the production of sulfonated lubricating agent for leather and tanned furs consisting of the steps of:

(a) sulfochlorinating higher fatty acids or esters of higher fatty acids having chain lengths of from 8 to 24 carbon atoms with chlorine and $SO_2$ at a temperature of from about 20° to 90° C. under UV-radiation for a time sufficient to obtain a compound having a chlorine content of from about 5 to 30 percent by weight and a content of $-SO_2Cl$ groups of from about 1 to 20 percent by weight, the ratio of chlorine atoms to $-SO_2Cl$ groups being from about 0.7:1 to 70:1; and (b) forming a water-emulsifiable alkali metal, ammonium, or lower alkyl-ammonium salt of the compound produced in step (a).

5 Claims, No Drawings

PREPARATION OF SULFONATED LUBRICATING AGENTS FOR LEATHER AND FURS

This application is a continuation of co-pending U.S. patent application Ser. No. 259,526, filed May 1, 1981, now abandoned.

FIELD OF THE INVENTION

This invention relates to sulfonated lubricating agents for leather and furs. More specifically, this invention relates of leathers and pelts that can be obtained in a substantially single-step reaction.

BACKGROUND OF THE INVENTION

In general, water-emulsifiable leather and fur fatting agents and lubricants are produced by sulfating unsaturated natural or synthetic fats, oils, or waxes with the usual sulfating agents, such as commercial sulfuric acid or oleum. As a rule, sulfation is continued only until sufficient emulsifiability is attained and the sulfation products obtained still have a considerable iodine number. However, the unsaturated character of these products unfavorably influences their oxidation stability and, hence, the shelf life of the lubricants as well as the light resistance of the leather and furs lubricated with them. Furthermore, the sulfuric acid esters formed by sulfation have little resistance to acid action in the leather and readily become saponified, thereby making it possible for free fatty acids to form and, if saturated fatty acids are present in sufficient quantity, fatty acid exudation to develop.

This drawback is eliminated, according to U.S. Pat. No. 3,370,005, by reducing the number of double bonds by 20 to 70 percent by partial chlorination of the unsaturated raw materials. The subsequent sulfation yields lubricants with improved properties regarding light resistance and shelf life, but even these products are sensitive to acid and not entirely stable in storage.

Leather lubricants are known from both U.S. Pat. No. 3,300,525 and French patent No. 2,031,167 which are obtained from sulfonation and, possibly partial chlorination of unsaturated natural or synthetic fatty acid esters. Sulfur trioxide, mixed with inert gases, if applicable, is used as the sulfonating agent. Due to their content of genuine sulfonates, such sulfonation products are acid-resistant. However, they retain a partially unsaturated character so that a degree of oxidation sensitivity and light sensitivity remains. Also, the sulfonation of unsaturated substances with sulfur trioxide is difficult because of the occurring strong oxidation reaction which makes it hard to prevent dark discolorations and undesired polymerizations. Not even a subsequent treatment of such sulfonates by means of the usual bleaching agents can eliminate the above disadvantages.

U.S. Pat. No. 3,988,247, incorporated herein by reference, discloses fat-liquoring agents for leather or furs based upon sulfonated chlorination products of natural or synthetic higher fatty acids or esters of fatty acids in the form of their alkali metal, ammonium, or amine salts. These agents consist of those sulfonated chlorination products that were obtained by chlorinating higher fatty acids or of esters of higher fatty acids having chain lengths of from 8 to 24 carbon atoms up to a chlorine content of from about 20 to 45 percent by weight, the products of chlorination generally not containing any olefinic double bonds, and subsequently sulfonating said products with $SO_3$ to attain an $SO_3$ content of from 40 to 150 mol, based on the products of chlorination.

OBJECTS OF THE INVENTION

It is an object of the invention to provide an improved procedure for preparing fat-liquoring agents for leathers or furs.

It is also an object of the invention to provide a substantially single-step reaction capable of producing effective sulfonated chlorination products for the fat-liquoring of leathers and furs.

It is a further object of the invention to provide a process for the production of a sulfonated lubricating agent for leather and tanned furs comprising sulfochlorinating higher fatty acids or esters of higher fatty acids having chain lengths of from 8 to 24 carbon atoms with chlorine and $SO_2$ at a temperature of from about 20° to 90° C. under UV-radiation for a time sufficient to attain a chlorine content of from about 5 to 30 percent by weight and a content of $SO_2Cl$ groups of from about 1 to 20 percent by weight, the ratio of chlorine atoms to $SO_2Cl$ groups being from about 0.7:1 to 70:1, followed by saponification.

These and other objects of the invention will become more apparent from the discussion below.

DETAILED DESCRIPTION OF THE INVENTION

It has now been found that effective sulfonated chlorination products for the liquoring of leather and tanned furs can be obtained in the form of their alkali metal, ammonium, or amine salts in a single step reaction where natural or synthetic higher fatty acids or esters of fatty acids are subjected to sulfochlorination with chlorine and sulfur dioxide. The basic reaction comprises sulfochlorinating higher fatty acids or esters of higher fatty acids having chain lengths of from 8 to 24 carbon atoms with chlorine and $SO_2$ at a temperature of from about 20° to 90° C. under UV-radiation for a time sufficient to attain a chlorine content of from about 5 to 30 percent by weight and a content of $SO_2Cl$ groups of from about 1 to 20 percent by weight, the ratio of chlorine atoms to $SO_2Cl$ groups being from about 0.7:1 to 70:1, which reaction is followed by saponification.

Until now, it was believed that the sulfochlorination reaction can be successfully applied only to paraffins and cycloparaffins (Rompps Chemie-Lexikon, 7th edition, pages 3398 and 3399). In contrast, the sulfochlorination of all products containing oxygen should proceed unfavorably (Lindner, Tenside, Textilhilfsmittel, Waschrohstoffe, Vol. I, p. 714, 1964). Consequently it is very surprising that the application of the sulfochlorination process to higher fatty acids or esters of higher fatty acids under the conditions described herein leads to effective fat-liquoring agents for leather and tanned furs whose effectiveness even surpasses that of the products of U.S. Pat. No. 3,988,247.

To produce the lubricants of the invention, it is preferred to start with naturally occurring higher fatty acids or esters of higher fatty acids having from 8 to 24, preferably 10 to 20, carbon atoms. Mixtures of fatty acids or fats or oils as present in naturally occurring aliphatic substances, especially those with a share of singly or repeatedly unsaturated fatty acids, are preferred. Preferably the starting material is a fatty acid compound selected from the group consisting of higher fatty acids having from 8 to 24 carbon atoms, esters of said higher fatty acids with alchohols selected from the group consisting of alkanols having 1 to 24 carbon atoms, alkanediols having 2 to 6 carbon atoms, alkanetriols having 3 to 6 carbon atoms, alkanetetraolso having from 4 to 6 carbon atoms and alkanehexaols having 6 carbon atoms, and naturally occurring fats, oils and waxes containing fatty acids having 8 to 24 carbon atoms. Examples of such fatty acid compounds are coconut oil, soybean oil, palm kernel oil, cottonseed oil, rapeseed oil, linseed oil, castor oil, sunflowerseed oil, olive oil, neat's foot oil, peanut oil, herring oil, cod liver oil, shark liver oil, whale oil, tallow fat or lard, furthermore the fatty acid mixture obtained from these fats or oils, and the naturally occurring wax esters such as sperm oil. Also, even aliphatic fatty acid compounds containing no unsaturated fatty acids or with a reduced content of unsaturated fatty acids, such as the saturated fats obtained by pressing, crystallization, or distillation, or partially or completely hardened fats or oils, can be utilized as starting materials.

Additionally suitable raw materials for the manufacture of lubricants according to the invention include synthetically produced esters of saturated or unsaturated fatty acids having from 8 to 24, preferably 10 to 20, carbon atoms, such as decanecarboxylic acid, palmitic acid, stearic acid, behenic acid, dodecenecarboxylic acid, oleic acid, linoleic acid or alkanoic acids produced by paraffin oxidation, with mono- or polyhydric aliphatic alcohols having from 1 to 6 carbon atoms, such as methanol, ethanol, isopropanol, butanol, ethyleneglycol, 1,2-propyleneglycol, glycerin, pentaerythrite or sorbitol, or higher alcohols having 8 to 24 carbon atoms, such as decylalcohol or oleylalcohol.

Due to their ready availability the natural animal or vegetable fats, oils or waxes are the products obtained from ester interchange with lower alkanols, in particular, methyl alcohol, and the corresponding fatty acid mixtures are preferred as raw materials.

The above-mentioned starting materials are sulfochlorinated by a well-known method by the simultaneous introduction of $Cl_2$ and $SO_2$ at a molar ratio of from about 85:1 to 1.4:1. The reaction temperature is from about 20° to 90° C. and is maintained at the desired level by cooling, if necessary A reaction temperature of from about 40° C. to 75° C. is preferred. The reaction is facilitated by radiation with UV-light (mercury vapor lamp). The reaction is complete after approximately 2 to 10 hours, after which time from about 5 to 30 percent by weight of chlorine and from about 1 to 20 percent by weight of $SO_2Cl$ groups have been added. The ratio of chlorine atoms to $SO_2Cl$ groups in the product of the reaction is from about 0.7:1 to 70:1, preferably from about 2:1 to 20:1, more preferably from about 3:1 to 7:1.

Subsequent saponification is performed with aqueous, approximately 30 percent sodium or potassium hydroxide solution at approximately 50° C., the neutralization being carried out either with an excess of the same alkali metal hydroxides or with ammonia solution or with an aliphatic or cycloaliphatic amine or an alkanolamine having from 2 to 6 carbon atoms, such as triethanolamine. Liquid, highly concentrated products that can be emulsified in water and have an excellent fastness to oxidation, light, and acid are obtained, which are eminently suitable for the lubrication or fat-liquoring of light-colored, pastel-tinted, and white leathers as well as for the fat-liquoring of valuable and delicate tanned furs.

If dark-colored or more unsaturated raw materials are used, bleaching the sulfonation products may be recommended. This is accomplished in the usual manner by adding small quantities of approximately 0.5 to 5 percent, preferably 1 to 4 percent, $H_2O_2$ solutions to the acid sulfonation product at temperatures of from about 20° and 80° C., preferably from about 40° and 60° C. Through this measure it is possible to lighten dark-colored sulfonatin products very considerably.

The products are used in the usual manner in the form of aqueous emulsions for the fat-liquoring or leather or for the treatment of furs. Preferably the sulfonated lubricants of the invention are applied to the leather and tanned furs by treating the leather in vats at a temperature of from about 40° to 80° C., preferably about 60° C., with a float or aqueous liquor of from about 80 to 250 percent, preferably from about 100 to 120 percent, containing from about 3 to 10 percent of the sulfonated lubricants of the invention, both based on the amount of the leather or tanned furs being treated.

The products of the invention are self-emulsifying so that the supplemental addition of emulsifiers is generally not required. However, to achieve specific effects, the sulfonation products may be combined with the corresponding unsulfonated chlorination products or other conventional leather treatment agents, such as unsulfonated oils or fats, for example, fish oil, sperm oil, neat's foot oil, and the like, or synthetic lubricants such as chloroparaffins, paraffin sulfonates, sulfated natural fats or oils or synthetic fatty acid esters, or mineral oils or the like, optionally in conjunction with anionic, nonionic, or cationic emulsifiers, preferably non-ionic surface-active compounds, such as ethylene oxide addition products to higher fatty alcohols, alkylphenols or alkylamines having 10 to 20 carbon atoms in the alkyl. Stabilization of the products may be accomplished by rendering hydrogen chloride residues possibly still present or newly formed harmless by means of epoxy compounds in amounts from 0.5 to 5 percent by weight. Pertinent examples are: glycide, epichlorohydrin, glycidyl ethers of mono- or polyhydric alcohols, such as glycol, glycerin, or sorbitol as well as epoxidized fats such as epoxidized soy bean oil, linseed oil or oleic acid butylester.

The products are well absorbed by the leather and yield excellent lubricating and softening action, with a remarkable resistance to water and aqueous or organic detergent solutions. Their tendency to migrate under thermal stress is minimal so that fusing operations or the vulcanization of rubber soles to shoe uppers can be carried out without difficulties. The good light, oxidation, and acid resistance of the sulfonated products of the invention, which also makes them suitable for the lubrication of sensitive and light-colored leathers and furs, is to be particularly emphasized. The treated leather or furs are characterized by their feeling especially pleasantly soft and oiled to the touch and by a beautiful glossiness of the fur.

The examples below are intended to illustrate the invention and should not be construed as limiting the invention thereto. The sulfochlorination reactions described in the examples were carried out in the following manner:

A glass reactor column filled with Raschig rings and enclosed by a double-jacket for heating and cooling liquid stood atop a 2 liter round-bottom flask having a bottom drain. The starting material was pumped through the bottom drain of the flask and then through a heatable rising tube into the head of the reaction column by means of a hose pump. The gases, chlorine and sulfur dioxide, were introduced through needle valves at the lower end of the column. Rotameters were used for the metering. The flow rate of the gases was from about 25 to 120 liters/hr for the chlorine and from about 4 to 50 liters/hr for the $SO_2$. The HCl gas produced was drawn off together with the rest of the unreacted starting gases through a washing bottle system at the head of the reaction column. The glass reaction column was irradiated from the outside with a mercury vapor lamp.

EXAMPLES

Example 1

One kilogram of tallow fatty acid ($C_{16}$–$C_{18}$) methyl ester was heated to 45° C. in the reactor and circulated with a hose pump at a rate of approximately 1 liter/hr. Chlorine (40 liters/hr) and $SO_2$ (7 liters/hr) were introduced in a counter-current into the reactor, irradiated from the outside by a mercury vapor lamp. The reaction, which was spontaneous, was evidenced by the formation of HCl vapor.

The reaction was complete after 220 minutes, and the reaction product (1350 gm) was freed of the dissolved gases (mainly HCl) under vacuum. The product contained 17 percent by weight of organically bound chlorine and 7.7 percent by weight of $SO_2Cl$ groups.

The saponification and neutralization was carried out with 300 gm of aqueous 30 percent NaOH at temperatures of from 40° to 50° C. The result was a stable emulsion that contained approximately 40 percent methyl ester sulfonate of chlorinated tallow fatty acid, 42 percent chlorinated tallow fatty acid methyl ester, and 18 percent inorganic salts and water.

Example 2

One kilogram of coconut oil fatty acid ($C_{12}$–$C_{18}$) methyl ester was reacted with 455 gm of chlorine (41.5 liters/hr) and 90 gm of $SO_2$ (9 liters/hr) within 3.5 hours at 40° C. under UV-irradiation. After removal of the dissolved gases, particularly HCl, under vacuum, 1319 gm of sulfochlorination product with a content of 14.4 percent by weight of chlorine and 8.5 percent by weight of $SO_2Cl$ were obtained.

An amount of 1.151 gm of the reaction product was saponified and neutralized with 268 gm of a 31 percent solution of sodium hydroxide. The homogenized product contained approximately 50 percent by weight of chlorosulfonated coconut oil fatty acid methyl ester, 30 percent by weight of chlorinated coconut oil fatty acid methyl ester, and 20 percent by weight of inorganic salts and water. The product formed a stable emulsion when diluted with water.

Example 3

One kilogram of palm kernel oil was treated with 410 gm of chlorine (26 liters/hr) and 123 gm of $SO_2$ (8.6 liters/hr) at 50° C. over 5 hours under UV-irradiation in the apparatus described. The product obtained was freed from gas under vacuum. The yield was 1340 gm of sulfochlorination product with a content of 13.4 percent by weight of chlorine and 10.5 percent by weight of $SO_2Cl$.

An amount of 1166 gm of the reaction product was saponified and neutralized with 421 gm of a 31 percent aqueous solution of sodium hydroxide at 50° C. The result was a stable emulsion with 30 percent by weight of chlorinated palm kernel oil and 28 percent by weight of inorganic salts and water.

Example 4

One kilogram of fancy tallow ($C_{16}$–$C_{18}$) was reacted in the same apparatus with 440 gm of chlorine (25.5 liters/hr) and 130 gm of $SO_2$ (8.5 liters/hr) at 50° C. over 5.5 hours and under VU-irradiation. After the removal of the gases, 1322 gm of the sulfochlorination product with a content of 15.4 percent by weight of chlorine and 9.7 percent by weight of $SO_2Cl$ were obtained.

Nine hundred and eighty grams of this product were hydrolyzed and neutralized at 50° C. with 261 gm of a 31 percent of sodium hydroxide. The resulting emulsion was stable and contained approximately 47 percent by weight of chlorosulfonated tallow, 31 percent by weight of chlorinated tallow, and 22 percent by weight of inorganic salts and water.

Example 5

Leather for uppers after-tanned with synthetic or vegetable or resin tanning agents, or with a combination of the mentioned tanning agents, was fat-liquored for 45 minutes at 60° C. in a vat with from 100 to 120 percent of bath solution and from 5 to 6 percent of the sulfochlorination product according to Example 2 as fat-liquoring substance, based upon the weight of the leather. The leathers, which were dried and finished by the conventional method, were characterized by a soft, supple, and full feel, good grain stability, as well as excellent fastness to light and oxidation.

Example 6

Chrome-tanned and dyed garment leather was fat-liquored in the vat for 45 minutes at 60° C. with from 100 to 120 percent of bath solution, from 7 to 10 percent of fat-liquoring substance consisting of a mixture of 80 percent by weight of the sulfochlorination product according to Example 1 and 20 percent by weight of a corresponding nonsulfonated but chlorinated tallow fatty acid methyl ester. The leathers, which were dried and finished by the conventional method, were characterized by a soft, supple, and full feel, as well as by excellent fastness to light and oxidation.

Example 7

Pastel-colored, chrome-tanned glove leather of lambs' skins were liquored in the vat for 45 minutes at 60° C. with 100 percent of bath solution and from 6 to 8 percent of fat-liquoring substance consisting of a mixture of 75 percent by weight of the sulfochlorination product according to Example 3, 21 percent by weight of chlorinated tallow fatty acid methyl ester that was not sulfonated, and 4 percent by weight of tallow fatty acid amine reacted with 4 mols of ethylene oxide, and then dried and finished by the conventional method. The leathers were characterized by an elastic, supple, soft feel and good light-fastness.

Example 8

Smoother neat's leather pickled in the usual manner was tanned with 8 percent of a commercial chrome-tanning agent with a content of 25 percent of $Cr_2O_3$ and 100 percent of bath solution and then pre-liquored in the same bath solution with 2 percent of fat-liquoring substance consisting of a mixture of 95 percent by weight of the sulfochlorination product according to Example 4, and 5 percent by weight of tallow fatty alcohol reacted with 20 mols of ethylene oxide. The upholstery leather that was tanned a second time by the usual method, dyed, and fat-liquored a second time with from 8 to 10 percent of the sulfochlorination product and then dried, was distinguished by a supple, soft feel and good light fastness.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the production of sulfonated lubricating agent for leather and tanned furs consisting of the steps of:
   (a) simultaneously sulfochlorinating esters of higher fatty acids having chain lengths of from 8 to 24 carbon atoms with chlorine and $SO_2$, the molar ratio of chlorine to $SO_2$ being from about 85:1 to 3:1, at a temperature of from about 40° to 75° C. under UV-radiation for a time sufficient to obtain a compound having a chorine content of from about 5 to 30 percent by weight and a content of $-SO_2Cl$ groups of from about 1 to 20 percent by weight, the ratio of chlorine atoms to $-SO_2Cl$ groups being from about 2:1 to 20:1; and
   (b) forming a water-emulsifiable alkali metal, ammonium, or lower alkyl-ammonium salt of the compound produced in step (a).

2. The process of claim 1, wherein the esters comprise naturally occurring mixtures of higher fatty acids having chain lengths of from 8 to 24 carbon atoms esterified with alcohols selected from the group consisting of alkanols having from 1 to 24 carbon atoms, alkanetriols having from 3 to 6 carbon atoms, alkanetetraols having from 4 to 6 carbon atoms, and alkanehexaols having 6 carbon atoms.

3. The process of claim 2, wherein the esters are methyl esters of fatty acids having chain lengths of from 10 to 20 carbon atoms.

4. The process of claim 1, wherein the ratio of chlorine atoms to $-SO_2Cl$ groups is from about 3:1 to 7:1.

5. A process for the production of sulfonated lubricating agent for leather and tanned furs consisting of the steps of:
   (a) simultaneously sulfochlorinating esters of fatty acids comprising naturally occurring mixtures of higher fatty acids having chain lengths of from 8 to 24 carbon atoms esterified with alcohols selected from the group consisting of alkanols having from 1 to 24 carbon atoms, alkanetriols having from 3 to 6 carbon atoms, alkanetetraols having from 4 to 6 carbon atoms, and alkanehexaols having 6 carbon atoms with chlorine and $SO_2$, the molar ratio of chlorine to $SO_2$ being from about 85:1 to 3:1, at a temperature of from about 40° to 75° C. under UV-radiation for a time sufficient to obtain a compound having a chlorine content of from 5 to 30 percent by weight and a content of $-SO_2Cl$ groups of from about 1 to 20 percent by weight, the ratio of chlorine atoms to $-SO_3Cl$ groups being from about 2:1 to 20:1; and
   (b) forming a water-emulsifiable alkali metal, ammonium, or lower alkyl-ammonium salt of the compound produced in step (a).

* * * * *